US008880163B2

(12) United States Patent
Barachant et al.

(10) Patent No.: US 8,880,163 B2
(45) Date of Patent: Nov. 4, 2014

(54) METHOD AND A SYSTEM FOR CLASSIFYING NEURAL SIGNALS, AND A METHOD OF SELECTING ELECTRODES FOR DIRECT NEURAL CONTROL

(75) Inventors: Alexandre Barachant, Grenoble (FR); Stéphane Bonnet, Lyons (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 304 days.

(21) Appl. No.: 13/180,739

(22) Filed: Jul. 12, 2011

(65) Prior Publication Data

US 2012/0071780 A1 Mar. 22, 2012

(30) Foreign Application Priority Data

Jul. 13, 2010 (FR) ..................................... 10 02948

(51) Int. Cl.

| | |
|---|---|
| ***A61B 5/04*** | (2006.01) |
| ***A61B 5/00*** | (2006.01) |
| ***A61B 5/0476*** | (2006.01) |
| ***G06K 9/00*** | (2006.01) |
| ***G06K 9/62*** | (2006.01) |
| ***G06F 3/01*** | (2006.01) |

(52) U.S. Cl.

CPC ........... *A61B 5/0476* (2013.01); *A61B 5/04012* (2013.01); *A61B 5/7267* (2013.01); *A61B 5/4064* (2013.01); *G06K 9/00536* (2013.01); *G06K 9/6234* (2013.01); *G06F 3/015* (2013.01)

USPC .......................................... 600/544; 600/545

(58) Field of Classification Search

USPC ................................................. 600/544, 545

See application file for complete search history.

(56) References Cited

U.S. PATENT DOCUMENTS

| | | | |
|---|---|---|---|
| 2007/0133878 | A1 | 6/2007 | Porikli et al. |
| 2008/0063264 | A1 | 3/2008 | Porikli et al. |
| 2008/0063285 | A1 | 3/2008 | Porikli et al. |

FOREIGN PATENT DOCUMENTS

WO WO 2009100654 A1 * 8/2009

OTHER PUBLICATIONS

Lotte, F. et al., *A Review of Classification Algorithms for EEG-Based Brain-Computer Interfaces*, Journal of Neural Engineering, vol. 4 (2007) pp. 1-24.

Moakher, M., *A Differential Geometric Approach to the Geometric Mean of Symmetric Positive-Definie Matrices*, SIAM J. Matrix Anal. Appl., 26 (2005) pp. 735-747.

Fisher LDA (Duda, R.O. et al.), *Pattern Classification*, Chapter 3.8.2, J. Wiley & Sons Inc., 2nd edition (2000) pp. 117-124.

(Continued)

*Primary Examiner* — Patricia Mallari
*Assistant Examiner* — Etsub Berhanu
(74) *Attorney, Agent, or Firm* — Alston & Bird LLP

(57) ABSTRACT

A classification method for classifying neural signals, the method comprising the following steps:

a) using a plurality of electrodes over a determined period of time to acquire a plurality of neural signal samples;
b) estimating a covariance matrix of said neural signals; and
c) classifying said neural signals, the classification being performed:
   either in the Riemann manifold of symmetric positive definite matrices of dimensions equal to the dimensions of said covariance matrix;
   or else in a tangent space of said Riemann manifold.

A method of selecting neural signal acquisition electrodes based on the Riemann geometry of covariance matrices of said signals. An application of said classification method and of said method of selecting electrodes to direct neural control.

14 Claims, 6 Drawing Sheets

(56) References Cited

OTHER PUBLICATIONS

Barachant, A. et al., *Filtrage Spatial Robuste á partir d'un sous-ensemble optimal d'électrodes en BCI EEG* (*Robust Spatial Filtering From an Optimum Subset of Electrodes in EEG BCI*),GRETSI 2009, Sep. 2009, 4 pages.
Barbaresco, F. et al., *Espace Riemannien symétrique et géométrie des espaces de matrices de covariance: :éequations de diffusion et calculs de médianes*, Actes Du Colloque Gretsi 2009, Sep. 8, 2009, pp. 1-4.
Barachant, A. et al., *Riemannian Geometry Applied to BCI Classification*, Latent Variable Analysis and Signal Separation, Proceedings of LVA/ICA 2010, Sep. 2010, pp. 629-636.
Barachant, A. et al., *Common Spatial Pattern Revisited by Riemannian Geometry*, Proceedings of 2010 IEEE International Workshop on Multimedia Signal Processing, Oct. 2010, pp. 472-476.
Gersch, W. et al., *A Kullback Leibler-Nearest Neighbor Rule Classification of EEGs: The EEG Population Screening Problem, An Anethesia Level EEG Classification Application*, Computers and Biomedical Research 13 (1980) pp. 283-296.
Kamousi, B. et al., *Classification of Motor Imagery by Means of Cortical Current Density Estimation and Von Neumann Entropy*, Journal of Neural Engineering 4 (2007) pp. 17-25.
Li, Y. et al., *EEG signal Classification Based on a Riemannian Distance Measure*, Proceedings of 2009 IEEE Toronto International Conference Science and Technology for Humanity ( 2009) pp, 268-273.
Search Report for French Application No. 10/02948 dated Jun. 16, 2011.
Li, Y., *Multichannel EEG Signal Classification on a Riemannian Manifold*, PhD thesis, Department of Electrical and Computer Engineering, McMaster University, Canada, Jan. 2011, 192 pages.

* cited by examiner

METHOD AND A SYSTEM FOR CLASSIFYING NEURAL SIGNALS, AND A METHOD OF SELECTING ELECTRODES FOR DIRECT NEURAL CONTROL

The invention relates to the technical field of direct neural control, or of brain-computer interfaces (BCI).

Brain-machine interfaces serve to establish communication between a user and a machine via neural signals coming from the activity of the subject's brain and without having recourse to using muscles, thereby constituting a genuine hope for people suffering from severe paralyses.

Usually, non-intrusive man-machine interfaces make use of electroencephalography (EEG) as a method of acquiring brain activity. A certain number of electrodes are placed on the surface of the head in order to measure electrical activity representative of the subject's brain activity. Other techniques that are more intrusive make use of electrocorticographic (ECoG) signals taken from the surface of the cortex, or indeed signals taken from deep electrodes.

In a man-machine interface, one or more mental tasks (actions imagined by the subject) are associated with one or more real actions by means of an effector. For example, imagining movement of the right hand may be associated with moving a cursor to the right. The fundamental problem that arises is thus that of detecting the performance of such mental tasks from among all of the brain activity that is measured; such detection then triggers actuation of the effector, which performs the desired action.

Detecting mental tasks (or imagined actions) generally comprises several steps. Firstly, filtering is applied to the "raw" neural signals in order to highlight frequency, time, or spatial characteristics that are specific to each mental task. Thereafter, "characteristics" are extracted from the signals as filtered in this way. Finally, a classification algorithm is applied to the characteristics. In other words, each set of characteristics corresponding to the neural signals acquired over a determined period (commonly referred to as an "epoch") is associated with a "class" that corresponds to a determined mental task, or to its negation. Thus, to move a cursor along a line it is necessary to have:

a first mental task (e.g. an imagined movement of the right hand) associated with a first direction of cursor movement (e.g. to the right);

a second mental task (e.g. an imaginary movement of the left hand) associated with a second direction of cursor movement (e.g. to the left); and three classes, corresponding to the first and second mental tasks, and also to any other form of brain activity that cannot be considered as constituting one or other of these two tasks.

The classification step relies on the characteristics extracted from a set of training data belonging to a class that is determined and known. A training data set may be written:

$$\{(x_1,y_1), \ldots ,(x_n,y_n)\}$$

where $x_i$ is the set of characteristics of the signal at instant $\underline{i}$ and $y_i$ is the associated class (and thus mental task). Training a "classifier" thus amounts to finding the following function:

$$h:X\rightarrow y$$

that maps the characteristics onto their classes. Classifying a point $\underline{x}$ thus amounts to calculating its class y=h(x). The quality of the function h( ) depends strongly on the quality of the characteristics used for calculating it. Thus, if the characteristics are very noisy, then the error rate is high. That is why the characteristics are generally not calculated on raw signals, but are extracted from signals that have previously been filtered.

The article by F. Lotte, M. Congedo, A. Lécuyer, F. Lamarche, and B. Arnaldi, "A review of classification algorithms for EEG-based brain-computer interfaces" Journal of Neural Engineering, Vol. 4, 2007, provides a summary of numerous methods of classification methods used in BCI.

The most commonly used method comprises:

a preprocessing step constituted by frequency filtering and spatial filtering using a common spatial pattern (CSP) method;

a step of extracting characteristics, which step consists in calculating the logarithm of the variance of the filtered signals; and a step of classification by performing Fisher's linear discriminant analysis (Fisher LDA) on the previously calculated characteristics.

That method generally provides good performance, is simple to use, and inexpensive in terms of calculation. However, it is not very robust (an outlier in the training data can easily corrupt the results), it requires a relatively large amount of training data, and it makes use of high-level characteristics that themselves require several kinds of preprocessing, in particular CSP, which is a supervised technique, which can be troublesome in certain applications, such as "non-supervised systems". Overall, it ceases to be very effective when there are more than two classes.

Spatial information is important in order to facilitate the classification of neural signals. Performing different mental tasks activates different regions of the brain, or activities the same regions but in different ways. In order to preserve a maximum amount of spatial information, it is common practice to use a large number of electrodes (up to about 100). That approach presents several drawbacks: inconvenience for the user, lengthy preparation time, and high calculation costs. In addition, certain types of processing reveal limitations when the number of electrodes increases (e.g. certain classifiers suffer from over-training).

Thus, techniques have been developed in order to optimize selection of a restricted number of electrodes.

Typically, a distinction is made between "bottom-up" selection in which a (small) optimum set of electrodes is built up progressively, "top-down" selection in which an optimum subset is selected from a set using a larger number of electrodes, and "top-down/bottom-up" selection which combines both of the preceding approaches. A distinction is also made between "patient-specific" selection in which an optimum set of electrodes is selected for a given user, and "application-specific" selection in which it is desired to determine a set of electrodes that is common to all users and that depends on the specific application, i.e. on the mental tasks that are to be detected.

For example, the article by A. Barachant, T. Aksenova, and S. Bonnet, "Filtrage spatial robuste partir d'un sous-ensemble optimal d'électrodes en BCI EEG" [Robust spatial filtering from an optimum subset of electrodes in EEG BCI] GRETSI 2009, Sep. 8-11, 2009, describes a bottom-up and patient-specific method of selecting electrodes based on a criterion of multiple correlations of the log-variance of signals after frequency filtering. The main drawbacks of that method lie in under-use of spatial information and in the relative complexity involved in implementing the algorithm.

The invention seeks to overcome the above-mentioned drawbacks of the prior art. In particular, the invention seeks:

firstly to provide a method of classifying neural signals—and particularly a multiclass classification method (i.e. a method involving more than two classes)—that is simultaneously robust, simple to implement, requires little training data, and requires few parameters to be adjusted; and secondly to provide a method of selecting electrodes for a direct neural interface that is simultaneously robust, simple, and flexible.

The classification method and the electrode selection method of the invention may be implemented independently of each other: one of the advantages of the selection method is specifically its flexibility, i.e. the possibility of combining it with other classification algorithms. Best results stem from using them in combination. However selecting electrodes on the basis of a Riemann distance criterion also greatly improves the performance of conventional classification methods, i.e. those implementing CSP filtering, since it imparts robustness to the filtering.

These methods are particularly suited to BCI using EEG signals, but that is not a fundamental limitation.

The classification method and the electrode selection method of the invention share a common approach, based on using covariance matrices of neural signals as "characteristics" that are descriptive of those signals. Those characteristics are relatively "close" to raw signals, thereby ensuring that the method is robust and achieving almost optimum use of the available information. Covariance matrices are matrices that may have a relatively large number of dimensions; it might therefore be thought difficult to use them as classifiers or in an electrode selection method. The invention overcomes that difficulty by the fact that the covariance matrices are symmetrical and positive definite; they can therefore be considered as being points of a Riemann manifold. The classifier and the electrode selection algorithm are thus based on the Riemann geometry of such a manifold. Having recourse to Riemann geometry is also found to be particularly advantageous in achieving good classification of the covariance matrices.

Document US 2008/0063285 describes a method of recognizing human figures in moving images based on the Riemann geometry of covariance matrices. That is a technical field that is quite different from BCI.

In a first aspect, the invention provides a classification method for classifying neural signals, the method comprising the following steps:

a) using a plurality of electrodes over a determined period of time to acquire a plurality of neural signal samples;

b) estimating a covariance matrix of said neural signals; and c) classifying said neural signals, the classification being performed:

either in the Riemann manifold of symmetric positive definite matrices of dimensions equal to the dimensions of said covariance matrix;

or else in a tangent space of said Riemann manifold.

In a preferred embodiment, said classification may be performed using a criterion based:

either on a Riemann distance defined on the Riemann manifold of symmetric positive definite matrices of dimensions equal to the dimensions of said covariance matrix; or else on a Euclidean distance defined on a tangent space of said Riemann manifold.

In particular embodiments of this method:

Said classification criterion may be a criterion of least Riemann distance between said covariance matrix of the signals to be classified and the symmetric positive definite matrices representing centers of the classes. In particular, each of said symmetric positive definite matrices representing the center of a class may correspond to the geometric mean or the median in said Riemann manifold of covariance matrices of training data associated with said class.

In a variant, said classification criterion may be a k nearest neighbors criterion in said Riemann manifold, between said covariance matrix of the signals that are to be classified and the covariance matrices of training data associated with the classes.

Before said classification step c), the method may include: determining a tangent space of said Riemann manifold relative to a symmetric positive matrix corresponding to a geometric mean or a median in said Riemann manifold of a set of covariance matrices of training data associated with classes; projecting said covariance matrix that needs to be classified together with said covariance matrices of training data into said tangent space; applying dimensional filtering in said tangent space; and back-projecting the filtered data into said Riemann manifold in order to perform said classification step c).

In a variant, said classification step c) may be implemented in a tangent space of said Riemann manifold, determined relative to a symmetric positive matrix corresponding to a geometric mean or to a median in said Riemann manifold of a set of covariance matrices of training data associated with classes. In particular, said classification step c) may be implemented by Fisher linear discriminant analysis in said tangent space.

More particularly, such a method may comprise: prior to said classification step c): determining a tangent space of said Riemann manifold relative to a symmetric positive matrix corresponding to a geometric mean or to a median in said Riemann manifold of a set of covariance matrices of training data associated with classes; projecting said covariance matrix that is to be classified together with said covariance matrices of training data into said tangent space; and applying dimensional filtering in said tangent space; and then implementing said classification step c) on the filtered data in said tangent space.

The method may include a step of preprocessing said neural signals by frequency filtering and centering.

Said neural signals may be electroencephalographic signals.

In a second aspect, the invention provides a direct neural control method comprising: a step of classifying neural signals as described above; and a step of generating a signal for controlling an apparatus as a function of the result of said classification step.

In a third aspect, the invention provides a system comprising: a set of neural signal acquisition electrodes; and a data processor device adapted to receive said signals and to use them for implementing a method as described above. The data processor device may be a computer—or a signal processor—that is suitably programmed for implementing the method, i.e. that is fitted with a memory that stores a program (a list of executable instructions) for implementing the method.

In a fourth aspect, the invention provides an electrode selection method for selecting neural signal acquisition electrodes for direct neural control, the method consisting in selecting a subset of electrodes or electrode locations from a set having a greater number thereof, so as to maximize the sum of the Riemann distances between covariance matrices representative of signals of different classes coming from said electrodes.

Such a method may in particular include the steps consisting in:

a) applying an initial set of neural signal acquisition electrodes to a subject;

b) using said electrodes and a plurality of determined periods to acquire a plurality of neural signal samples, the signals corresponding to each period being associated with one out of a plurality of classes;

c) estimating a covariance matrix of the neural signals from each period, each of said covariance matrices being considered as a point of a Riemann manifold;

d) for each of said classes, calculating a symmetric positive definite matrix representing a class center; and e) selecting a subset of said electrodes in such a manner as to maximize the sum of the Riemann distances between said centers of the classes.

This constitutes top-down selection.

In various particular implementations of this method:

Said step d) may consist in calculating the geometric mean or the median in said Riemann manifold of the covariance matrices of the signals associated with each class.

Said step e) may be implemented iteratively and on each iteration includes eliminating an electrode that is selected in such a manner as to minimize the decrease in the Riemann distance between the mean or median covariance matrices of said classes that results therefrom.

In a variant (bottom-up selection), the selection method may include the steps consisting in:

f) determining a set of locations for applying neural signal acquisition electrodes on a subject; and g) progressively applying electrodes so as to maximally increment some sum of the Riemann distances between the covariance matrices representative of different classes of signals from said electrodes. In other words, at each increment, the electrode is added that maximizes the increase in the Riemann distance between said covariance matrices.

Regardless of whether selection is bottom-up or top-down:

The method may lead to determining a subset of electrodes having a predetermined number of elements.

Each class of neural signals may correspond to an action imagined by the subject.

Each of said electrodes may be adapted to acquire neural signals generated by a determined region of the subject's brain.

In a fifth aspect, the invention provides a method of selecting neural signal acquisition electrodes for direct neural control, the method comprising: implementing a (bottom-up or top-down) selection method as described above on a plurality of subjects with the same initial set of electrodes or locations for electrodes for all of the subjects, so as to determine a subset of electrodes for each subject; and selecting electrodes of said initial set that belong to the greatest number of said subsets.

In a sixth aspect, the invention provides a direct neural control method as described above, including a prior operation of selecting neural signal acquisition electrodes as described above.

Other characteristics, details, and advantages of the invention appear on reading the following description made with reference to the accompanying drawings given by way of example and in which.

Figure 1:
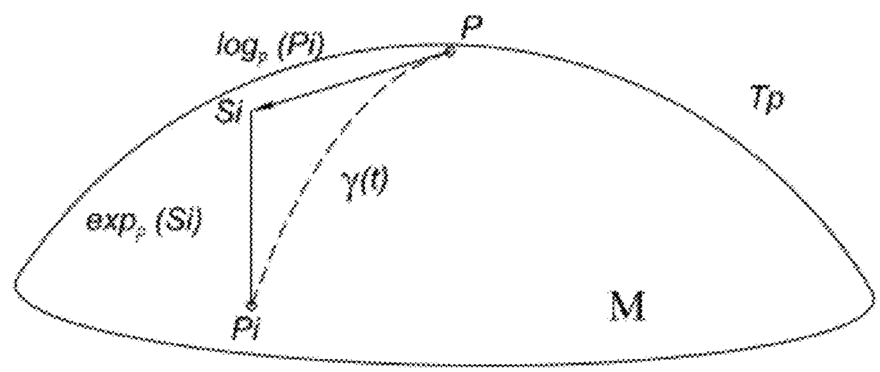
FIG. 1 is a diagram illustrating the concepts of Riemann manifold, geodesic, Riemann distance, and tangent space.

It is appropriate to begin by defining several fundamental notions of Riemann geometry with reference to FIG. 1.

A Riemann manifold is a topological space that is locally homeomorphic to a Euclidean space ($R^n$) that is differentiable, and over which a scalar product is defined that is sufficiently regular. The scalar product makes it possible in turn to define a geometry (a "Riemann" geometry) on the Riemann manifold. This geometry does not coincide with "usual" Euclidean geometry; that is why in FIG. 1 the Riemann manifold M is represented (symbolically) by a curved surface.

A symmetric positive definitive (SPD) matrix is a square matrix that is symmetrical about its diagonal ($a_{ij}=a_{ji}$) and that has eigenvalues that are strictly positive. An SPD matrix of dimensions n×n has n(n+1)/2 independent elements; it may therefore be represented in a space of n(n+1)/2 dimensions. It is possible to show that this space may have the structure of a Riemann manifold. Below, consideration is given solely to the manifolds M of SPD matrices having dimensions n×n, where n is naturally greater than 1.

The Riemann distance between two points $P_1$ and $P_2$ of the Riemann manifold M may be defined by:

$$\delta_R(P_1, P_2) = \|\mathrm{Log}(P_1^{-1}P_2)\|_F = \left[\sum_{i=1}^{n}\log^2\lambda_i\right]^{1/2}$$

where $\|\cdot\|_F$ is the Frobenius norm and $\lambda_i$ are the eigenvalues of $P_1^{-1}P_2$ (real and strictly positive). The logarithm of an SPD matrix "P" is given by:

$$\mathrm{Log}(P)=V\log(D)V^{-1}$$

where V is the matrix of the eigenvectors of P, D is the diagonal matrix of its eigenvalues, and log(D) represents the diagonal matrix of the logarithms of the eigenvalues of P.

This definition of the Riemann distance is not univalent. Other metrics equivalent to $\delta_R$ may be defined on the manifold M. For example, an alternative distance suitable for use in implementing the invention is defined by:

$$\|\mathrm{Log}(P_1)-\mathrm{Log}(P_2)\|_F$$

A geodesic is the shortest path on the manifold M between two points $P_1$ and $P_2$. It is defined in parametric form, using the parameter $t\in[0,1]$ as follows:

$$\gamma(t) = P_1^{1/2}(P_1^{-1/2}P_2P_1^{-1/2})^t P_1^{1/2}$$

Corresponding to each point P of the Riemann manifold M, it is possible to define—in univalent manner—the tangent space $T_p$ that is a Euclidean space (represented symbolically by a plane in FIG. 1). More precisely, given a point P of the manifold M, it is possible to for each other point $P_i$ of the manifold to define the tangent vector:

$$S_i=\dot{\gamma}(0)$$

where γ is the geodesic between P and $P_i$, and where the dot represents the differentiation operation.

The manifold M is locally (around the point P) homeomorphic to the tangent space $T_p$ constituted by the set of tangent vectors $S_i$. Each point $P_i$ of the Riemann manifold M can therefore be associated with a point $S_i$ of the tangent space $T_p$ (i.e. a tangent vector) by a projection operation that is generally referred to as a "log map", defined as follows:

$$\text{Log}_P(P_i)=P^{1/2}\,\text{Log}(P^{-1/2}P_iP^{-1/2})P^{1/2}$$

Conversely, going from the tangent space to the manifold M is performed by means of an "exp map" operation:

$$\text{Exp}_P(S_i)=P^{1/2}\text{Exp}(P^{-1/2}S_iP^{-1/2})P^{1/2}$$

The power t in the SPD matrix "P" is defined by:

$$P^t=VD^tV^{-1}$$

where V is the matrix of the eigenvectors of P, D is the diagonal matrix of its eigenvalues, and $D^t$ is the diagonal matrix of the eigenvalues of P raised to the power t.

At the point P, the elements of the tangent space of the Riemann manifold of SPD matrices having dimensions n×n are symmetric matrices of the same dimensions, but in general they are not positive definite matrices.

Another useful concept for the description below is that of a geometric mean in the Riemann sense, of m SPD matrices belonging to the manifold M:

$$\mathfrak{G}(P_1, \ldots , P_m) = \underset{P\in P(n)}{\text{argmin}}\sum_{i=1}^{m}\delta_R^2(P, P_i)$$

where P(n) represents the set of n×n SPD matrices.

There is no analytic formula that makes it possible to calculate this mean; it is therefore necessary to have recourse to iterative algorithms.

The simplest of these algorithms consists in:

1) Determining a first estimate $P^0_\Omega$ of the geometric mean in order to initialize the algorithm; for example, it is possible to take the arithmetic mean of the matrices.

2) Projecting the matrices $P_1 \ldots P_m$ into the tangent space at the point $P^0_\Omega$ (it should be observed that the term "point" and "matrix" are used interchangeably depending on whether emphasis is being put on aspects that are geometric or algebraic).

3) Calculate the arithmetic mean S of the projections of the matrices, and then return to the Riemann manifold by applying an exp map. This provides a new estimate $P^1_\Omega$ of the mean (more generally, at iteration i, the estimate is written $P^1_\Omega$).

4) Steps 2 and 3 are iterated, each time using the tangent space at the point $P^{i-1}_\Omega$ as determined at the preceding iteration. The process comes to an end when the Frobenius norm of the matrix S (geometric mean in the tangent space) as calculated in step 3 is less than a threshold value.

There also exist algorithms that make it possible to calculate robust estimators of the mean. For further details concerning the Riemann geometry of SPD matrices, reference may be made to the article by M. Moakher "A differential geometric approach to the geometric mean of symmetric positive-definite matrices" SIAM J. Matrix Anal. Appl., 26, 2005.

As explained above, the invention starts from the assumption that the covariance matrices of neural signals—and in particular of EEG signals—constitute good indicators of a subject's brain activity and can be used for implementing direct neural interfaces, providing these matrices are considered as points of a Riemann manifold, thus making it possible to preserve structure and relationships.

Figure 2:
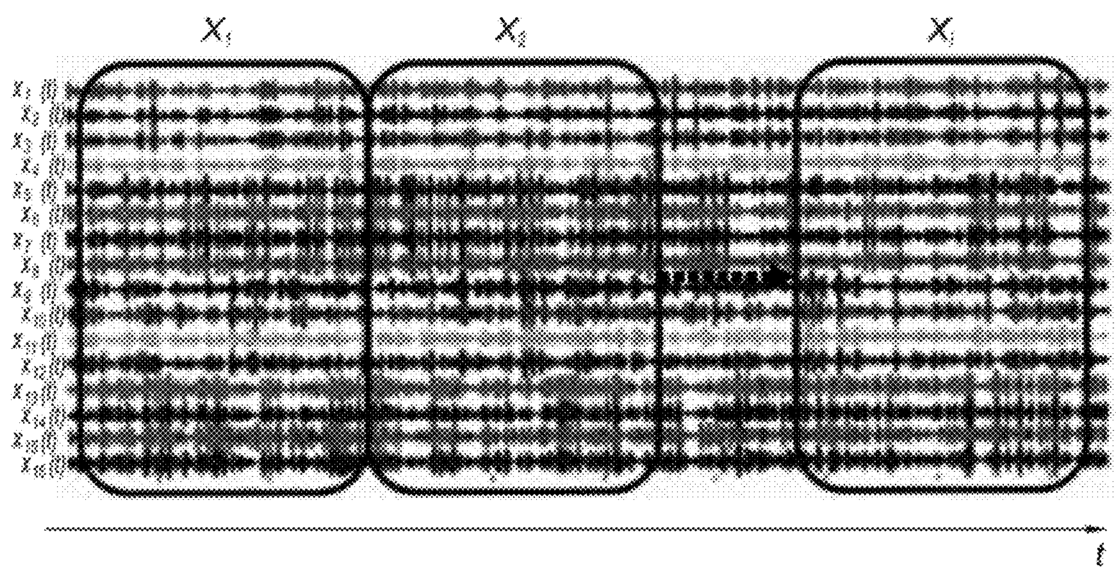
FIG. 2 shows the subdivision of neural signals implemented by the classification and electrode-selection methods of the invention.

FIG. 2 explains the concept of a "covariance matrix of neural signals". A subject, or patient, or user (these terms are used interchangeably herein) is fitted with N electrodes for EEG or ECoG. Each electrode i delivers a signal $x_i(t)$ as a function of time. This signal is sampled so as to operate in discrete time: $x_{ij}=x_i(t_j)$, and then digitized. This produces a matrix representation of the set of neural signals. The overall acquisition time is subdivided into periods, known in the art as "epochs". Each epoch is thus associated with a matrix $X_1$, $X_2, \ldots, X_I$ representative of the signals acquired during said epoch. In practice, these matrices generally correspond to frequency-filtered signals, in order to improve the signal-to-noise ratio and isolate a spectral region of interest, and they are centered by subtracting the mean, as calculated on a row-by-row basis (in reality, the "centering" is an automatic consequence of filtering when the filtering eliminates the DC component of the signal). The covariance matrix $P_i$ of the $i^{th}$ epoch may be estimated as follows:

$$P_i = \frac{1}{M-1}X_iX_i^T$$

where M is the number of samples in the epoch for each electrode (not to be confused with M, which is the Riemann manifold). Other estimators that are robust and known in themselves may equally well be used.

Figure 3:
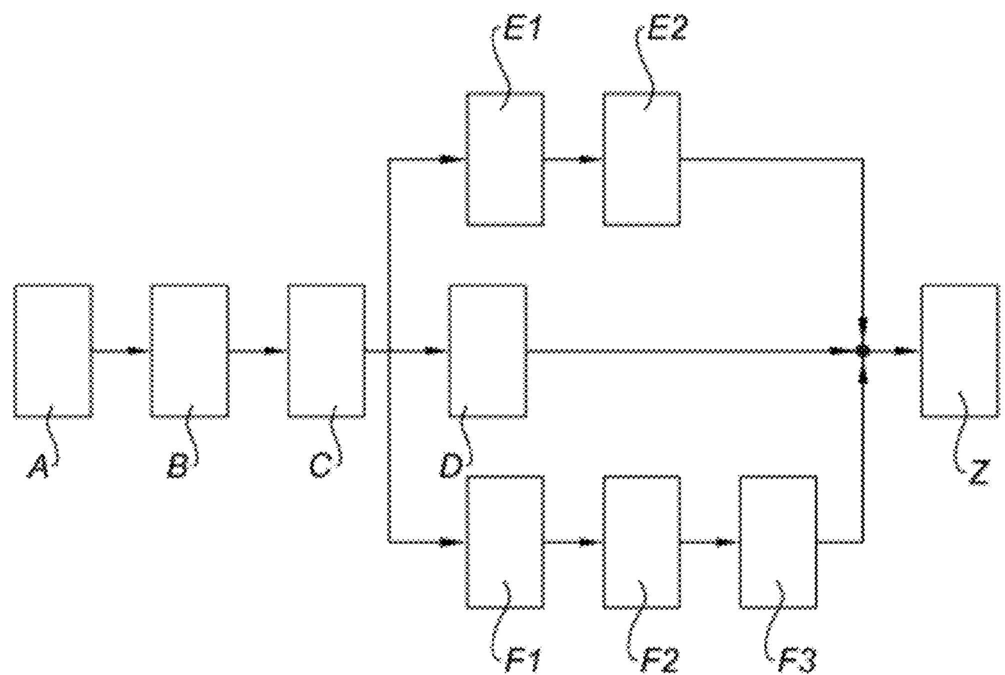
FIG. 3 is a flow chart showing different variants of the classification method of the invention.

FIG. 3 is a general flow chart of a method of the invention.

Step A consists in acquiring the neural signals using a set of electrodes (it is explained below how to determine this set in optimum manner).

Step B comprises conventional preprocessing operations: sampling; analog-to-digital conversion; filtering; centering; normalizing; . . . .

Step C consists in estimating covariance matrices associated with different epochs, considered as being points of a Riemann manifold M.

Step D consists in classifying the covariance matrices in said Riemann manifold. The classifier is generated from training data, i.e. from covariance matrices of epochs belonging to known classes (periods during which the subject has performed a predefined mental task).

Finally, step Z consists in generating control signals for controlling an effector on the basis of the results of the classification. The classification of neural signals may be used for purposes other than BCI (research, diagnosis, . . . ), in which case it is possible to omit said step Z.

Steps E1 and E2 may be implemented as an alternative to step D. They consist in:

E1: projecting the covariance matrices into a tangent space (generally the point corresponding to the geometric mean in the Riemann sense of the training data); and E2: classifying in said tangent space.

This alternative approach is advantageous in that it makes it possible to apply "sophisticated" classifiers that cannot be used directly in a Riemann manifold, such as Fisher's linear discriminant analysis (LDA).

An alternative to step E2 is constituted by F1, F2, F3:

F1 consists in applying a "dimensional filtering" operation in the tangent space. The "dimensional filtering" differs from dimensional reduction in that the dimensions of the data are kept constant by filling with zeros;

F2 consists in projecting the dimensionally filtered data into the original Riemann manifold ("exp map"); and finally F3 consists in classifying the dimensionally filtered data in the Riemann manifold.

Figure 4:
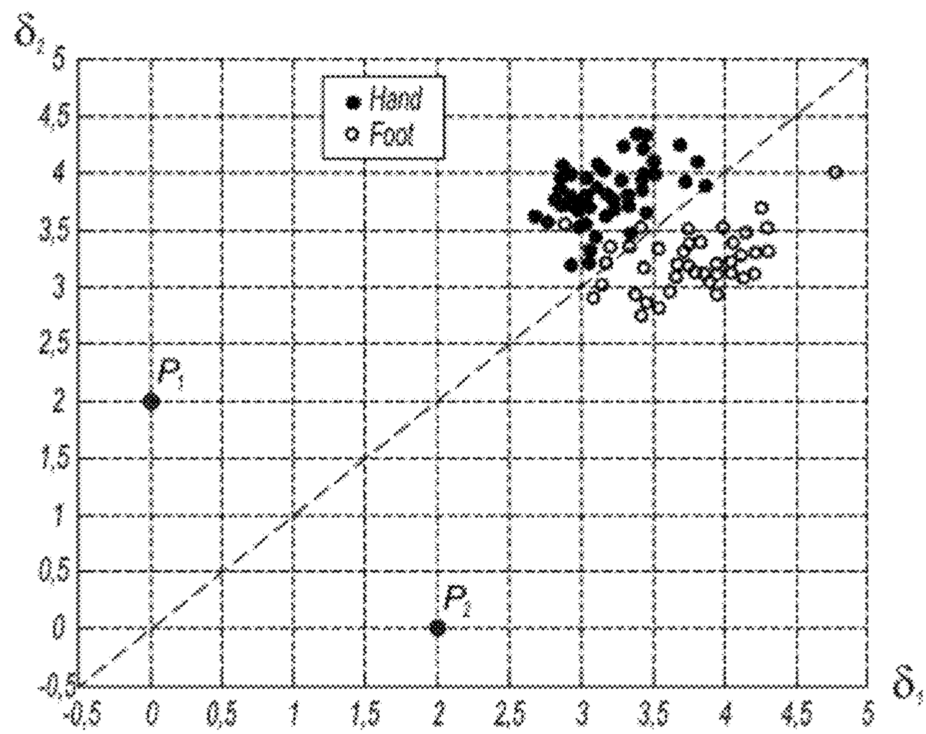
FIG. 4 is a graph illustrating a classification method in a first implementation of the invention, based on measuring the Riemann distance relative to the mean.

FIG. 4 shows a first method of classifying neural signals in a Riemann manifold: the method is referred to as the "distance to the mean" (or "distance to the median"). The principle consists in defining, on the Riemann manifold, so-called "class center" points (matrices). There is one—and only one—such point for each class. FIG. 4 shows two such points $P_1$ and $P_2$ that correspond to two distinct mental tasks: imagining moving a hand and imagining moving a foot. The Riemann distance $\delta_1(P_i)$, or $\delta_2(P_i)$ is calculated between each covariance matrix of an epoch of cerebral activity that is to be classified and the corresponding point $P_1$ or $P_2$. If $\delta_1(P_i)$ is less $\delta_2(P_i)$, then $P_i$ is associated with class No. 1 (moving the hand), otherwise it is associated with class No. 2 (moving the foot). FIG. 4 shows representations of $P_1$ and $P_2$ together with several covariance matrices for classifying in a $\delta_1/\delta_2$ plane. The "real" classification of these covariance matrices is known: the dark points correspond to epochs during which the subject imagined moving the hand (these points should therefore be associated with the first class); the pale points correspond to epochs during which the subject imagined moving the foot (these points should therefore be associated with the second class). It can be seen that the classification is correct for the great majority of points.

There arises the problem of determining the "class centers". One way of proceeding is as follows. Several training signals are acquired: these are covariance matrices of epochs of cerebral activity for which the real classification is known (imagined movement of the hand or of the foot). The points that represent these matrices form "clouds" in the Riemann manifold M. The point $P_1$ is defined as the geometric mean (in the Riemann sense) of the covariance matrices of the training signals that correspond to an imagined movement of the hand (and thus of training matrices belonging to the first class). The point $P_1$ is defined as the geometric mean (in the Riemann sense) of the covariance matrices of the training signals corresponding to an imagined movement of the hand (and thus of the training matrices belonging to the first class). In a variant, the class center $P_1$ may correspond to the median of the covariance matrices of the training signals. The median in the Riemann manifold is defined as the point that minimizes the sum of the Riemann distances (and not their squares). It may be determined by an iterative algorithm, like the mean; however convergence is more difficult to achieve for this algorithm.

In the mean (median) distance method, the training data serves solely to calculate the "class centers", after which it may be forgotten. In an alternative method, referred to as the "$\underline{k}$ nearest neighbors" method, the data continues to play a pivotal role. In this method, for each "point" of the Riemann manifold corresponding to a covariance matrix that is to be classified, the $\underline{k}$ "points" are determined that correspond to the training matrices that are the closest in the Riemann sense. In general, these "$\underline{k}$ nearest neighbors" belong to different classes. The point that is to be classified is allocated to the class to which the majority of the $\underline{k}$ nearest neighbors belong.

Figure 5:
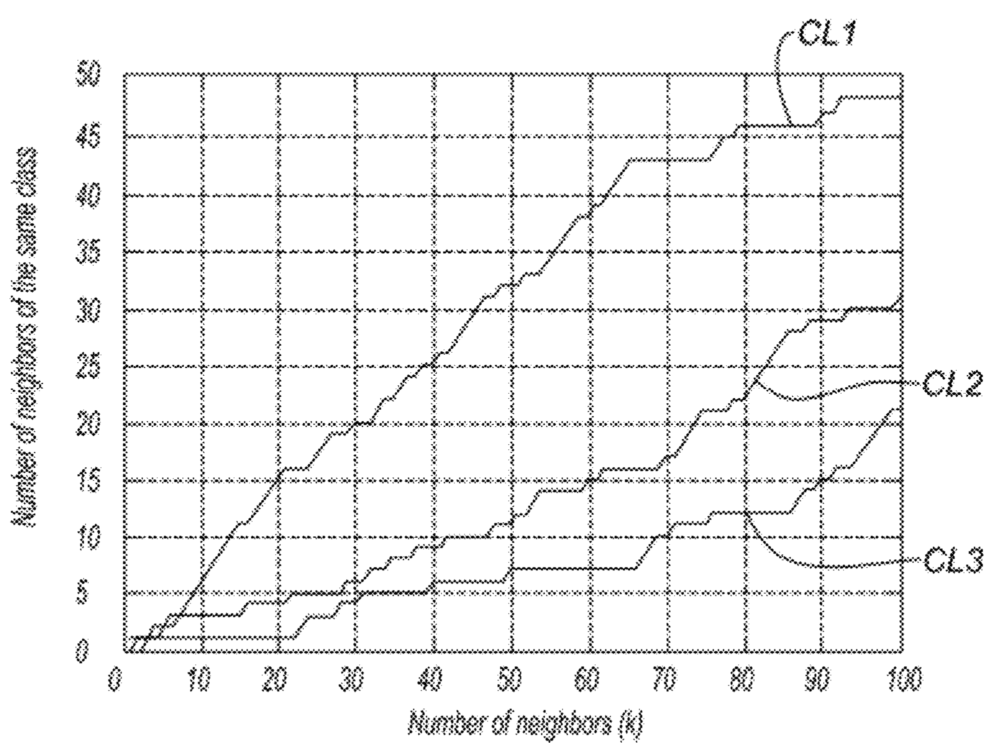
FIG. 5 is a graph showing a classification method in a second implementation of the invention, based on the criterion of the k nearest neighbors (in the Riemann sense)
Figure 6:
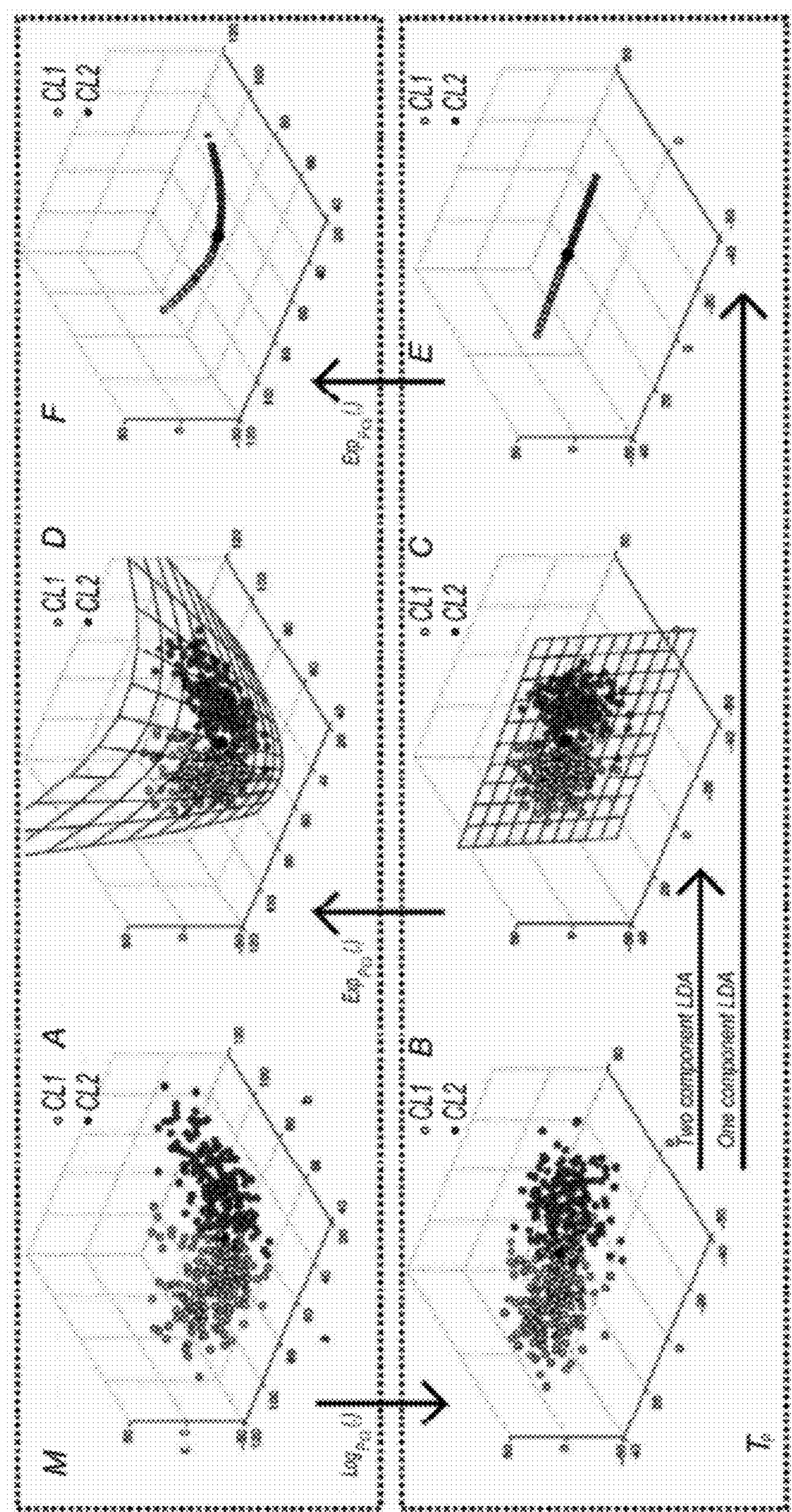
FIG. 6 illustrates various classification methods in respective implementations of the invention, including a projection of classification data into a space that is tangential to the Riemann manifold of the covariance matrices.

In the example of FIG. 5, 100 training points are used that are associated with three classes ("hand": CL1, "foot": CL2, "rest": CL3). Consideration is given to classifying an epoch of cerebral activity that is known to be associated with an imagined movement of the hand. The abscissa axis represents the number $\underline{k}$ of nearest neighbors taken into consideration; the ordinate axis represents the number of nearest neighbors per class. It can already be seen that for k=10, the epoch is allocated in non-ambiguous manner to the correct category.

The examples of FIGS. 4 and 5 correspond to branch D of the flow chart of FIG. 3 (direct classification in the Riemann manifold). Consideration is now given to the E1, E2 branch, i.e. classification in the tangent space.

It is known that the Riemann manifold M possesses a tangent space for each of its points. The question thus arises of determining the tangent space into which the data should be projected in order to be classified. In order to minimize the distortion of the data caused by projection, it is preferable to select the tangent space that relates to the geometric mean of the training data. In a variant, it is possible to select the tangent space relating to the median of the training data.

Each "point" (SPD matrix) Pi of the Riemann manifold M corresponds to a "point" Si in the tangent space under consideration. However, $S_i$ is a matrix that is symmetrical only. There is therefore information redundancy in its coefficients. The following operation is introduced:

$$\tilde{S}_i=\mathrm{vect}(S_i)$$

consisting in retaining only the coefficients in the top portion of the matrix and arranging them in the form of vectors, as illustrated by the following example for a 3×3 matrix:

$$S_i=\begin{bmatrix}1&2&3\\2&4&5\\3&5&6\end{bmatrix}\xrightarrow{vect}\tilde{S}_i=\begin{bmatrix}1\\2\\3\\4\\5\\6\end{bmatrix}$$

where $S_i$ is a matrix of dimension n×n, $\tilde{S}_i$ and is a vector of n*(n+1)/2 elements.

A new data set is thus created in which a classifier is trained:

$$\{(\tilde{S}_1,Y_1)\ldots(\tilde{S}_i,Y_i)\ldots(\tilde{S}_{180},Y_{180})\}$$

where $Y_i$ is the "real" class of the training vector $\tilde{S}_i$.

By way of example, this classifier may be a Fisher linear discriminant analysis.

Unfortunately, there is a difficulty. The vectors $\tilde{S}_i$ are of size n*(n+1)/2, and when the number of electrodes becomes large (of the order of 20 or more), the size of these vectors approaches the total number of points in the database (generally 200 to 500 in BCI), or exceeds this number. Conventional LDA or regression type algorithms tolerate this poorly and lead to over-training. For LDA in particular, the solution is not possible if the size of the vectors exceeds the number of points of the data set. Use is then made either of dimension reduction or of regularization methods. These methods form an integral portion of the state of the art for classification techniques. A simple regularization method consists in artificially increasing the number of data points in the training database, either by resampling said data, or by introducing noise (each point is duplicated and moved a little by applying Gaussian white noise).

By way of example, dimensional reduction may be performed by Fisher LDA (R. O. Duda, P. E. Hart, D. G. Stork "Pattern classification", Chapter 3.8.2, pp. 117-124, J. Wiley & Sons Inc., 2nd edition, 2000). This method projects data onto vectors arranged in a hierarchy by size, with only a number K being conserved (where K is generally small compared with the total dimension of the data); projection onto a single vector may be considered as binary classification (the sign of the projection gives the belonging class directly). At this point, it is possible to perform classification in the tangent space, or to return to the Riemann manifold. To do this, it is necessary to return to a data representation that has the original dimensions; however the values of dimensions other than the K dimensions retained after Fisher LDA are set to be equal to zero. Since there is no reduction proper in the number of dimensions, the term "dimensional filtering" is used.

FIG. 6 shows:

A) Data of two different classes (pale points and dark points) in a three-dimensional Riemann manifold, corresponding to SPD matrices having dimensions 2×2 (naturally, this is merely an example for visualization purposes; the covariance matrices used in BCI have many more dimensions, but that is not easily visualized). The classification may be performed directly in the Riemann manifold.

B) The projection of this data into a tangent space. The "curvature" of the Riemann manifold is lost, since the tangent space is Euclidean. Classification may be performed in the tangent space.

C) A two-component Fisher LDA is applied. The data is flattened onto a plane (a two-dimensional Euclidean space), that is selected in such a manner as to optimize the separation of the classes. It is possible to perform classification in this Euclidean space having a reduced number of dimensions.

D) By considering that the plane obtained at point C) is immersed in the three-dimensional tangent space, it is possible to return to the Riemann manifold. The data for classifying is arranged on a surface (generally a hypersurface) of the Riemann manifold.

E) Starting from point B), it is possible to apply a Fisher LDA to one component. The data is concentrated on a line corresponding to the direction of the greatest separation of the classes. Classification is particularly easy, but information is lost. This loss of information may be acceptable when classification is to be performed on two classes; in contrast, using only one component is generally not sufficient for multiclass classification.

F) Starting from point E), it is possible to return to the Riemann manifold. The belonging data is concentrated onto a line, and more precisely onto a geodesic (the geodesic of the greatest separation between the classes).

Consideration is given below to a specific example of a brain-machine interface that uses 16 EEG electrodes and that involves three mental tasks: moving a hand, moving a foot, and resting. The training data for the classifier is obtained by asking the user to perform each of the mental tasks 20 times over for a period of 3 seconds per task. The neural signals are sampled at 512 hertz (Hz), filtered by a bandpass filter in the range 8 Hz to 30 Hz, and then subdivided into 1-second epochs (there are thus 180 of them), and for each of which a covariance matrix $X_i$ is determined. Each of these covariance matrices—having dimensions 16×512—is associated with a scalar $Y_i$ that indicates the corresponding mental task: 1 for moving the hand; 2 for moving the foot; and 3 for rest.

This data is used with various types of classifier:

a "conventional" process: CSP followed by multiclass LDA;

classification by distance from the mean in the Riemann manifold of the matrices $X_i$;

classification by the k closest neighbors (k=20) in the Riemann manifold of the matrices $X_i$; and classification by LDA in the tangent space;

with this being done for nine users U1 to U9.

These results, expressed as a percentage of correct classification, are given in the following matrix. The last row but one gives the mean results, and the last row the improvement compared with the reference method. It should be understood that random classification would give a result equal to 33.33%.

| User | Reference (CSP + LDA) | Distance to the mean | k closest neighbors | LDA in tangent space |
|---|---|---|---|---|
| U1 | 34.9 | 55.0 | 51.0 | 49.7 |
| U2 | 48.3 | 61.6 | 57.6 | 51.7 |
| U3 | 44.7 | 44.1 | 36.2 | 40.8 |
| U4 | 73.4 | 76.0 | 73.4 | 67.1 |
| U5 | 50.0 | 58.4 | 57.1 | 50.7 |
| U6 | 38.5 | 67.1 | 62.1 | 62.8 |
| U7 | 31.5 | 37.0 | 39.5 | 30.9 |
| U8 | 55.5 | 58.7 | 55.5 | 44.6 |
| U9 | 65.4 | 57.7 | 64.7 | 64.2 |
| Mean | 49.1 | 57.3 | 55.2 | 51.4 |
| Improvement (%) | | +8.2 | +6.1 | +2.3 |

Classification methods based on Riemann geometry provide a significant improvement in performance, except for LDA in tangent space that, under the conditions considered above, is close to over-training (with 16 electrodes, the $\tilde{S}_i$ are of dimension 136, which is close to the number of training points, i.e. 180).

The classification methods considered above are of the "supervised" type, i.e. they make use of training signals, each of known class. The invention also applies to non-supervised classification methods, even though they are generally more difficult to use in BCI. By way of example, mention may be made of the Riemann generalization of the k-means method that is itself known. A non-supervised method of the invention for classifying neural signals comprises the following steps:

a) acquiring neural signals over I epochs in time, and after optional preprocessing, determining the covariance matrices;

b) randomly allocating each covariance matrix—considered as a point of a Riemann manifold—to one out of k classes;

c) calculating the center in the Riemann sense (geometric mean or median) for each class; and d) calculating the Riemann distance between each matrix and the k centers of the classes; thereafter each matrix is reallocated to the class of center that is the closest;

then iteratively repeating steps c) and d) until convergence is achieved.

When a new "point" (a new acquisition epoch) arises, it is possible to restart the algorithm on the increased data set. In a variant, it is possible to fix the class centers definitively after a (non-supervised) training stage, and to make use merely of a classification by distance from the mean (median) for data that is acquired subsequently.

The use of the Riemann manifold in non-supervised classification techniques serves to make good advantage of spatial information even though CSP filtering is not available (since that requires supervision).

Above, it has been assumed that the set of electrodes (the number of electrodes, and their arrangement on the user's head) is a given. In reality, those are parameters that can be adjusted in order to optimize BCI performance. Riemann geometry of the covariance matrices of neural signals is found to be useful not only for classification proper, but also for determining how to arrange signal acquisition electrodes.

The general idea is to select a certain number of electrodes from a more numerous set, in such a manner as to maximize the Riemann distance between the centers of the training data classes (or more generally between the matrices that "represent" the various classes). If there are more than two classes, a search is made to maximize a function of distances between the class centers taken in pairs, typically, use is made of their sum:

$$\text{Criterion} = \sum_{k=1}^{K-1} \sum_{j>k}^{K} \delta_R(P_k, P_j)$$

where $\delta_R$ the Riemann distance, $P_k$ and $P_j$ are the centers of the classes, and the sum is extended to all pairs of classes.

Adding an electrode increases the number of dimensions of the matrices X, and therefore of the Riemann manifold; in general this gives rise to an increase in the distance between the centers of the classes. If no such increase occurs, that means that the added electrode does not provide any information that is useful for classification. Conversely, removing an electrode, in general, reduces the distances between the class centers. If this reduction is large, that means that the removed electrode was providing a large amount of useful information (and therefore that it ought probably to have been conserved). If the reduction is small or zero, that means that the electrode was contributing little useful information (and thus that eliminating it makes it possible to simplify the system without significantly degrading its performance).

This approach is particularly suitable for top-down selection. The procedure is as follows:

It starts with a "complete" set having a large number N of electrode, and training signals are acquired.

Thereafter, the covariance matrices are calculated, the class centers are determined, and the "criterion" is calculated (the sum of the differences between said class centers).

Thereafter consideration is given to all subsets of N−1 electrodes (each obtained by eliminating one electrode from the complete set). The new covariance matrices and the new value for the "criterion" are calculated for each of these subsets. The subset that presents the highest value for the "criterion" is retained; that is the subset obtained by eliminating from the complete set the electrode that contributed the least information that was useful for classification purposes.

And so on: at each step, all of the subsets obtained by eliminating one electrode are verified and the best of those subsets is selected (i.e. the subset that optimizes the criterion defined by the distance between the centers of the classes). This technique ensures that, at each step, the electrode that is eliminated is the least "useful" of the remaining electrodes.

The selection process comes to an end when a predefined number of electrodes remain; or else when the value of the "criterion" drops below a threshold (e.g. 80% of its initial value).

Figure 7:
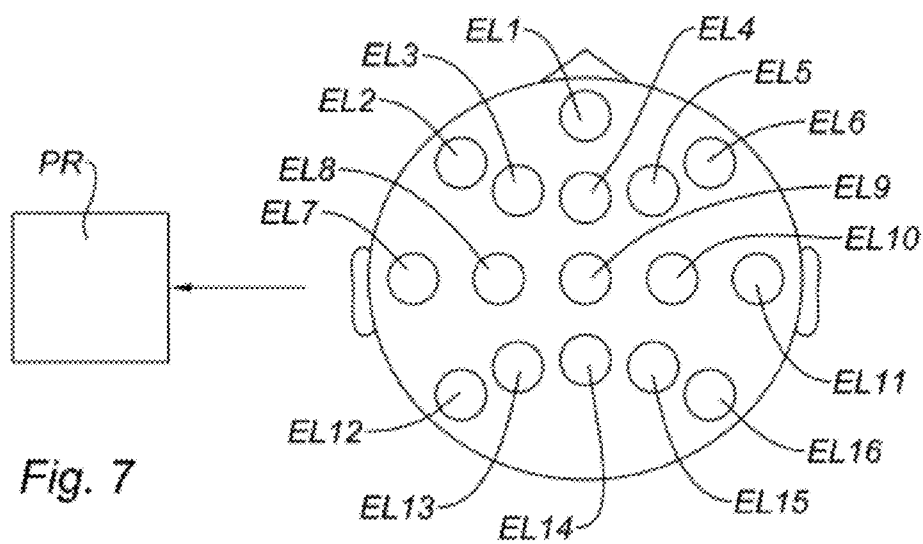
FIG. 7 shows the implantation layout for 16 EEG electrodes for a BCI.

By way of example, FIG. 7 shows an initial layout of 16 electrodes EL1 to EL16, which number is to be reduced in optimum manner. As in the example described above, when illustrating various methods of classifying neural signals, three mental tasks are taken into consideration (moving a hand, a foot, and resting) together with the training data obtained by asking the user to perform each of three mental tasks 20 times over for a duration of 3 seconds per task. The neural signals are sampled at 512 Hz, filtered by a 8 Hz to 30 Hz bandpass filter, and then subdivided into 1-second epochs.

FIG. 7 also shows in diagrammatic manner a processor PR programmed to implement a classification and BCI method as described above.

Figure 8:
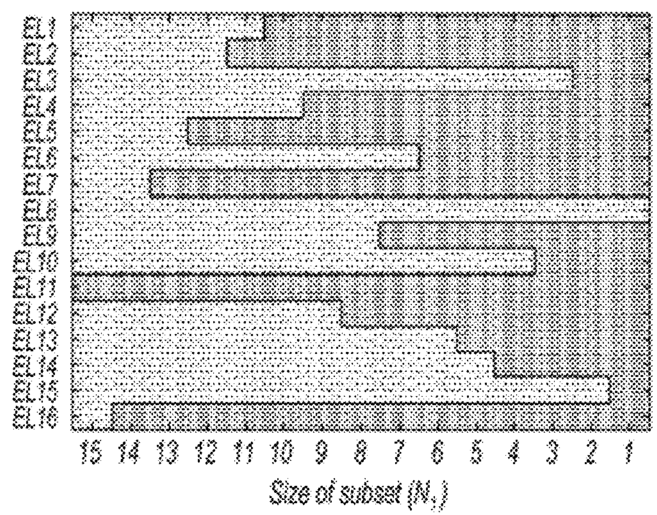
FIGS. 8 and 9 show the application of a patient-specific electrode-selection method to the implantation layout of FIG. 7.

FIG. 8 shows how selection proceeds: the ordinate axis represents the electrodes and the abscissa axis represents the size of the subset; pale gray indicates an electrode that is conserved while dark gray indicates an electrode that is eliminated. It can be seen that the electrode EL11 is the first to be eliminated, followed by electrode EL16, and so on. The optimum subset using three electrodes for the user in question comprises the electrodes EL3, EL8, and EL15. If only one electrode were to be retained, it would be EL8.

Figure 9:
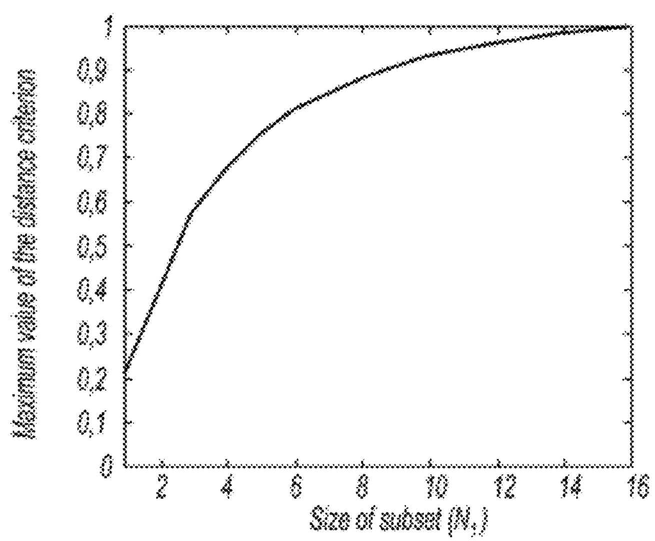

FIG. 9 shows how the maximum value of the distance criterion varies as a function of the size of the subset of electrodes. It can be seen that going from 16 electrodes to ten gives rise to a moderate reduction of said value (of the order of 10%). In contrast, it would be very penalizing to use fewer than three electrodes.

This method is simple and robust. Its simplicity comes in particular from the fact that the covariance matrices corresponding to the various subsets of electrodes can be calculated immediately once they have been calculated for the complete set.

In the covariance matrices, the information contributed by electrode i is represented by the $i^{th}$ row and the $i^{th}$ column. Consequently, in order to determine the covariance matrices corresponding to the subset of (N-1) electrodes obtained by removing the electrode i, it suffices to take the covariance matrices of the complete set of N electrodes and to remove the $n^{th}$ row and the $n^{th}$ column therefrom.

More generally, it is possible to define the following "red cov" operation:

$$P \xrightarrow[S]{\text{red cov}} \tilde{P}$$

where P is a covariance matrix, S is a vector containing the indices of the electrodes to be conserved, and $\tilde{P}$ is the reduced covariance matrix. For example, if S=[3,7], then:

$$P = \begin{bmatrix} p_{1,1} & \cdots & p_{N,1} \\ \vdots & \ddots & \vdots \\ p_{1,N} & \cdots & p_{N,N} \end{bmatrix} \xrightarrow[S=[3,7]]{\text{red cov}} \tilde{P} = \begin{bmatrix} p_{3,3} & p_{7,3} \\ p_{3,7} & p_{7,7} \end{bmatrix}$$

This means that calculating the covariance matrices corresponding to the subsets with reduced numbers of electrodes can be performed merely by eliminating rows and columns from the covariance matrices corresponding to the complete set.

Figure 10:
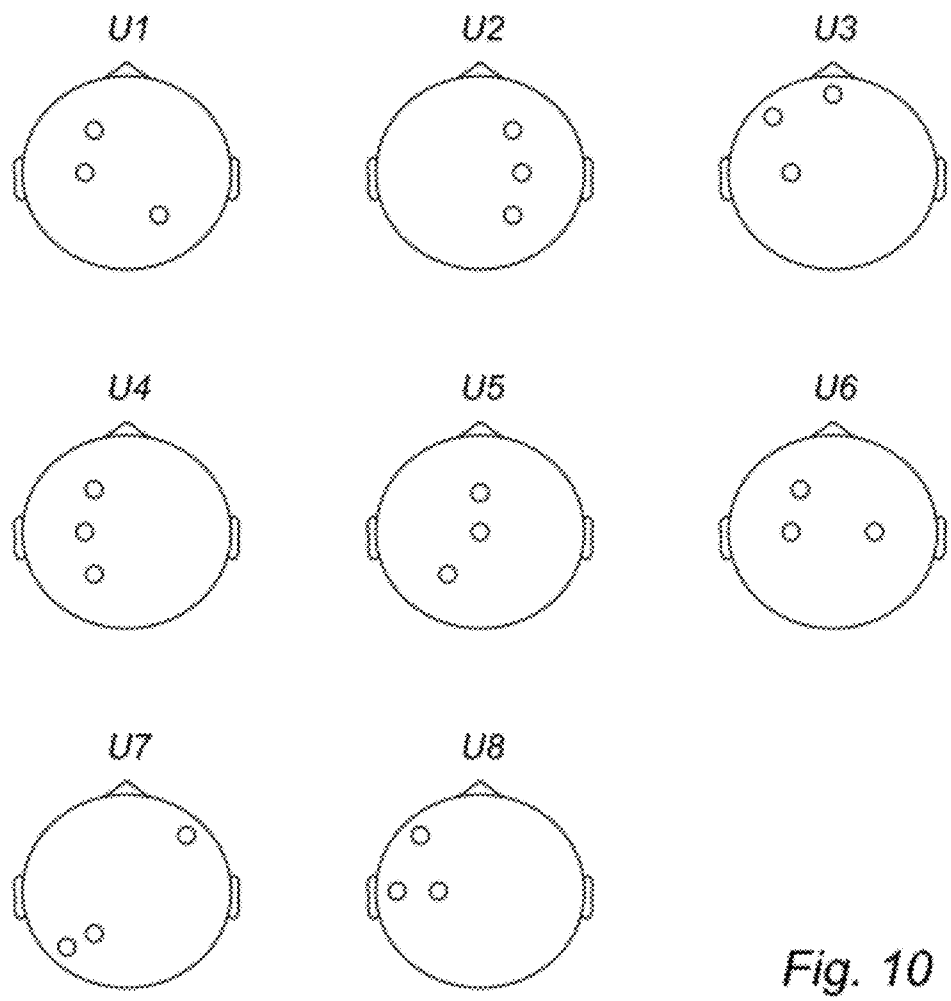
FIG. 10 shows the results of the same method applied to eight different users.

The above-described method makes "patient-specific" selection possible: if it is applied to several different subjects, then different "optimum" subsets of electrodes will be obtained. This is shown in FIG. 10, which shows the "optimum" subsets for eight users U1-U8.

It is possible to combine this "patient-specific" selection with "application-specific" selection: quite simply, electrodes are selected that appear most frequently in the optimum subset for the various users. Thus, in FIG. 9, it can be seen that the electrode EL8 is selected for five users, that the electrodes EL3 and EL13 are selected for three users, while the other electrodes are selected for two, one, or zero users.

Figure 11:
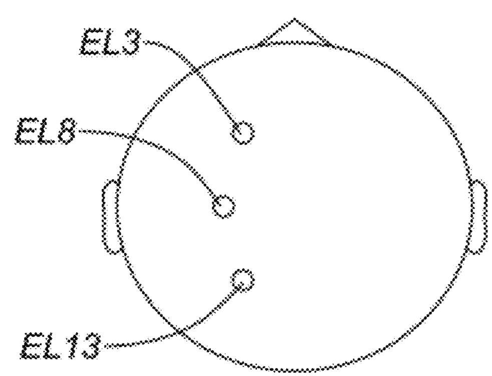
FIG. 11 shows the application of an "application-specific" electrode-selection method to the users of FIG. 10.

The optimum three-electrode subset that may be assumed to be satisfactory for most users, is therefore constituted by the electrodes EL3, EL8, and EL13. This subset is shown in FIG. 11.

It is also possible to perform bottom-up selection by proceeding as follows. The selection starts with a predefined set of possible locations for the electrodes (see FIG. 7). It begins by putting a single electrode into place, and testing all available locations while measuring, for each location, the distance (or some of the distances) between the class centers. The electrode is identified that corresponds to the greatest distance, and an electrode is left at that location. At this point all of the remaining locations are tested with a second electrode, and so on (it should be observed that during the first iteration, the "covariance matrix" is in reality a scalar, or a 1×1 "matrix"). This serves to select an optimum subset of locations for electrodes for each user. The "application-specific" selection is performed in exactly the same manner as for the top-down selection (see FIGS. 10 and 11).

In a manner that is itself known, it is also possible to combine bottom-up selection with top-down selection.

The invention claimed is:

1. A classification method for classifying neural signals, the method comprising the following steps:

a) acquiring a plurality of neural signal samples ($x_1(t)$-$x_{16}(t)$) over a determined period of time using a plurality of electrodes (EL1-EL16); and using a data processor device:

b) estimating a covariance matrix ($P_i$) of said neural signals associated with the determined period of time and considered as a point of the Riemann manifold of symmetric positive definite matrices of dimensions equal to the dimensions of said covariance matrix; and c) classifying said neural signals, the classification being performed:

either in the Riemann manifold of symmetric positive definite matrices of dimensions equal to the dimensions of said covariance matrix;

or else in a tangent space of said Riemann manifold.

2. A classification method according to claim 1, wherein said classification is performed using a criterion based:

either on a Riemann distance defined on the Riemann manifold of symmetric positive definite matrices of dimensions equal to the dimensions of said covariance matrix; or else on a Euclidean distance defined on a tangent space of said Riemann manifold.

3. A classification method according to claim 2, wherein said classification criterion is a criterion of least Riemann distance between said covariance matrix ($P_i$) of the signals to be classified and the symmetric positive definite matrices ($P_1$, $P_2$) representing centers of a plurality of classes.

4. A classification method according to claim 3, wherein each of said symmetric positive definite matrices representing the center of a class corresponds to the geometric mean or the median in said Riemann manifold of covariance matrices of training data associated with said class.

5. A classification method according to claim 2, wherein said classification criterion is a k nearest neighbors criterion in said Riemann manifold, between said covariance matrix of the signals that are to be classified and the covariance matrices of training data associated with the classes.

6. A classification method according to claim 1, including, prior to said classification step c):

determining a tangent space of said Riemann manifold relative to a symmetric positive matrix corresponding to a geometric mean or a median in said Riemann manifold of a set of covariance matrices of training data associated with classes;

projecting said covariance matrix that needs to be classified together with said covariance matrices of training data into said tangent space;

applying dimensional filtering in said tangent space; and back-projecting the filtered data into said Riemann manifold in order to perform said classification step c).

7. A classification method according to claim 1, wherein said classification step c) is implemented in a tangent space of said Riemann manifold, determined relative to a symmetric positive matrix (P) corresponding to a geometric mean or to a median in said Riemann manifold of a set of covariance matrices of training data associated with classes.

8. A method according to claim 7, wherein said classification step c) is implemented by Fisher linear discriminant analysis in said tangent space.

9. A classification method according to claim 7, comprising:

prior to said classification step c):

determining a tangent space of said Riemann manifold relative to a symmetric positive matrix corresponding to a geometric mean or to a median in said Riemann manifold of a set of covariance matrices of training data associated with classes;

projecting said covariance matrix that is to be classified together with said covariance matrices of training data into said tangent space; and applying dimensional filtering in said tangent space; and then implementing said classification step c) on the filtered data in said tangent space.

10. A method according to claim 1, including a step of preprocessing said neural signals by frequency filtering and centering.

11. A method according to claim 1, wherein said neural signals are electroencephalographic signals.

12. A direct neural control method comprising:

a step of classifying neural signals in accordance with claim 1; and a step of generating a signal for controlling an apparatus as a function of the result of said classification step.

13. A direct neural control method according to claim 12, including a prior operation of selecting neural signal acquisition electrodes comprising selecting a subset of electrodes or electrode locations from a set having a greater number thereof, so as to maximize the sum of the Riemann distances between covariance matrices representative of signals of different classes coming from said electrodes.

14. A system comprising:

a set of neural signal acquisition electrodes (EL1-EL16); and a data processor device (PR) adapted to receive said signals and implement a method according to claim 1.

* * * * *

UNITED STATES PATENT AND TRADEMARK OFFICE

CERTIFICATE OF CORRECTION

PATENT NO. : 8,880,163 B2
APPLICATION NO. : 13/180739
DATED : November 4, 2014
INVENTOR(S) : Barachant et al.

It is certified that error appears in the above-identified patent and that said Letters Patent is hereby corrected as shown below:

Title page,
Item (75) Inventors: "Stéphane Bonnet, Lyons (FR)" should read --Stéphane Bonnet, Lyon (FR)--.

Signed and Sealed this
Fourteenth Day of April, 2015

Michelle K. Lee

Michelle K. Lee
*Director of the United States Patent and Trademark Office*